United States Patent [19]

Stokes

[11] Patent Number: 4,711,251
[45] Date of Patent: Dec. 8, 1987

[54] BODY IMPLANTABLE LEAD

[75] Inventor: Kenneth B. Stokes, Minneapolis, Minn.

[73] Assignee: Medtronic, Inc., Minneapolis, Minn.

[21] Appl. No.: 480,913

[22] Filed: Mar. 31, 1983

Related U.S. Application Data

[63] Continuation of Ser. No. 182,963, Sep. 2, 1980, abandoned.

[51] Int. Cl.4 .............................................. A61N 1/04
[52] U.S. Cl. ................................. 128/784; 128/419 P; 128/786; 604/892
[58] Field of Search ............... 128/419 P, 784–786; 604/892

[56] References Cited

U.S. PATENT DOCUMENTS

| | | | |
|---|---|---|---|
| 3,568,660 | 3/1971 | Crites | 128/419 P |
| 3,680,544 | 8/1972 | Shinnick | 128/419 P |
| 4,055,178 | 10/1977 | Harrigan | 604/892 |
| 4,281,668 | 8/1981 | Richter et al. | 128/784 |

*Primary Examiner*—William E. Kamm
*Attorney, Agent, or Firm*—Vidas & Arrett

[57] ABSTRACT

A body implantable lead for the delivery of stimulation energy to a desired body site including a drug dispenser carried by the lead which retains a drug to be dispensed while allowing a dispensing of that drug at least adjacent the desired body stimulation site. The drug may be one which is intended to counter thrombus formation, fibrosis, inflammation or arrhythmias, or any combination thereof, or to accomplish any other localized purpose. The drug may be in liquid form retained in a reservoir carried by the lead with an agency controlling dispensing of the drug. The controlling agency may be a semi-permeable membrane. Alternatively, the reservoir may be formed as an osmotic pump. As a further alternative, the drug may be retained as a coating on a large surface area portion of the lead, or an electrode carried by the lead. In a preferred embodiment, the drug is compounded into a solid material which is carried by the lead while being exposed to body tissues and flesh or fluids at least adjacent the desired stimulation site.

3 Claims, 6 Drawing Figures

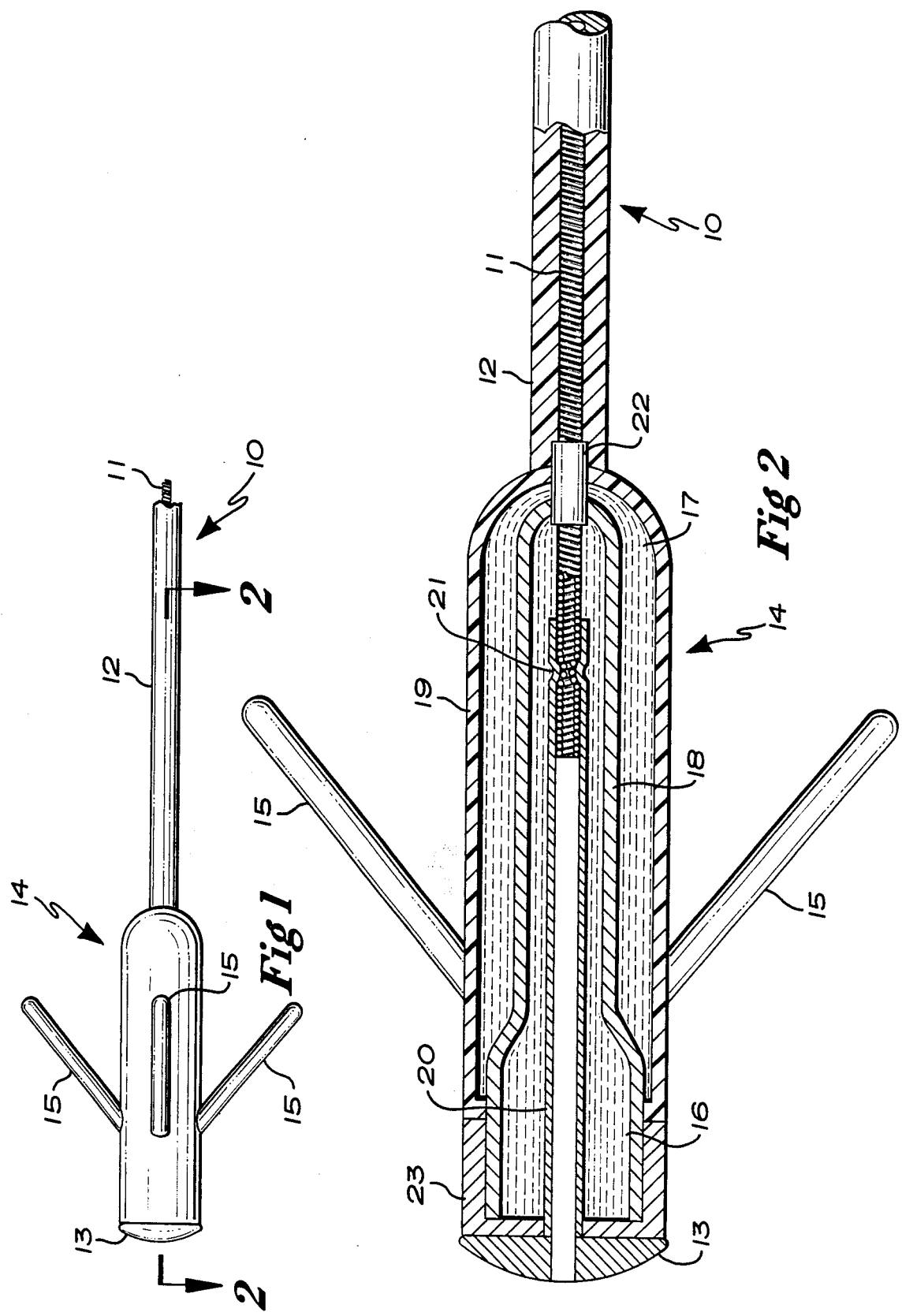

BODY IMPLANTABLE LEAD

This is a continuation of application Ser. No. 182,963, filed Sept. 2, 1980 and now abandoned.

DESCRIPTION

1. Background of Prior Art

Electrical stimulation of the body for medical purposes is well known in the prior art. An example of a device for this purpose is the well-known cardiac pacemaker. In the pacemaker context, as well as other body stimulation contexts, the stimulation is delivered to the desired body site by an electrode carrying lead.

Interactions between the lead and body can vitiate the desired effects of the stimulation. For example, material reactions may encourage fibrosis. In the pacemaking context, fibrosis is believed to be a major factor in the increase in chronic threshold that is usually experienced. Also, mechanical trauma may result in inflammation of the tissue to be stimulated. Such inflammation may alter the response of the tissue to the stimulation energy, both acutely and chronically.

Other interactions between the lead and body, while not directly affecting the response of the tissue to the stimulation energy, can result in the occurrence of undesirable events. In some circumstances where electrical body stimulation is indicated, the body portion to be stimulated is irritable. The placement of a lead may compound this irritability. For example, the placement of a pacemaking lead may induce a cardiac arrhythmia. The presence of the lead may also promote thrombus formation.

The interactions noted above have long been recognized and efforts made to ameliorate their consequences. For example, the lead may be configured to reduce mechanical trauma and the response of irritable tissue during lead placement. Materials may be selected for the lead body and electrodes to minimize fibrosis. Thrombus formation may also be countered by the administration of suitable drugs. It is also known that a systemic treatment with steroids results in acute reduction in the threshold level.

The administration of drugs to counter the undesirable interactions between the lead and body noted above has not gained widespread acceptance in that it has heretofore required a systemic treatment to counter a localized interaction. Also, lead configuration must take into account other factors such as the efficiency of the delivery of the stimulation energy, the ease of lead placement, maintenance of the desired electrode position and reliability of the lead over extended periods of time. An accommodation of these interests has resulted in leads whose configuration necessarily results in undesirable interactions between the lead and body.

2. Brief Summary of the Invention

The present invention provides a body implantable lead for the delivery of stimulation energy to a desired body site which may be configured and constructed in accordance with known techniques while ameliorating the effects of undesirable interactions between the lead and body. A drug dispenser is carried by the lead and includes a member for retaining the drug to be dispensed while allowing a dispensing of that drug at least adjacent the desired body stimulation site. The drug may be one intended to counter thrombus formation, fibrosis, inflammation, or arrhythmias, or any combination thereof, or to accomplish any other desirable localized purpose. The drug may be retained in liquid form in a reservoir including an agency for controlling the dispensing of the drug. The agency may be a semipermeable membrane or, alternatively, the reservoir may be formed as an osmotic pump. The drug may be carried as a coating on a high surface area portion of the lead, or an electrode carried by the lead. In a preferred embodiment, the drug is compounded into a solid material with that solid material being carried by the lead adjacent the electrode. Most preferably, the lead carries a tip electrode at its distal end with the drug being dispensed through the tip electrode.

BRIEF DESCRIPTION OF THE DRAWINGS

FIG. 1 illustrates a portion of a body implantable lead constructed in accordance with a preferred embodiment of the present invention.

FIG. 2 illustrates a cross-section taken along the line 2—2 in FIG. 1.

DETAILED DESCRIPTION OF THE INVENTION

Figure 3:
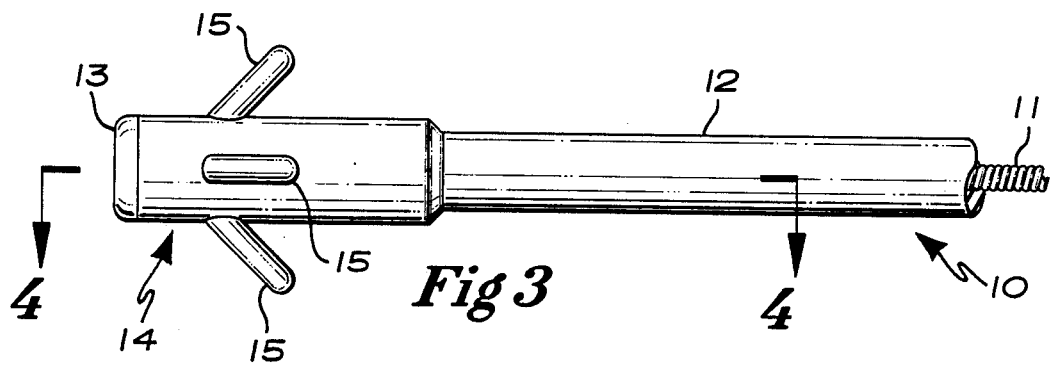
FIG. 3 illustrates the configuration of a portion of a lead constructed in accordance with the preferred embodiments illustrated in FIGS. 4–6.

FIG. 1 illustrates a portion of a lead constructed in accordance with a preferred embodiment of the present invention including a lead body 10 formed of a conductor 11 and insulating sheath 12 and carrying at its distal end a tip electrode 13. The conductor 11 extends between the tip electrode 13 and a source of stimulation energy, in known manner. In the illustrated embodiment, the conductor 11 is formed as a helically wound conductor, also in known manner. A drug dispenser indicated generally at 14 is carried by the lead and has tines 15 extending therefrom. Tines 15 are of known design and form no part of the present invention aside from forming a portion of the disclosed preferred embodiments thereof.

FIG. 2 is a cross-section taken along the line 2—2 in FIG. 1 and illustrates drug dispenser 14 as an osmotic pump of generally known design. Pump 14 has inner and outer chambers 16 and 17, respectively, separated by an impermeable membrane 18. A semi-permeable membrane 19 forms the outer wall of chamber 17 while an extension 20 of electrode 13 extends into the chamber 16. As is apparent to those skilled in the art, the electrode 13 and its extension 20 are formed of a conductive material.

The conductor 11 extends from the lead body 10 into the chamber 16 and into electrical communication with the extension 20 of electrode 13. The extension 20 of electrode 13 may be crimped as at 21 to maintain the electrical communication between it and the conductor 11. A seal 22 is provided in the chamber walls 18 and 19 at the point at which the conductor 11 passes through them. An end cap 23 closes the chamber 16.

Prior to implantation, the chamber 16 is charged with a drug to be dispensed. The drug may be any suitable drug intended to accomplish any desirable localized purpose. For example, the drug may be one intended to counter thrombus formation, fibrosis, inflammation, or arrhythmias, or any combination of drugs intended to accomplish one or more of those purposes, or any drug or combination of drugs intended to accomplish any other desirable localized purpose or purposes. The chamber 16 is charged through the extension 20 of electrode 13 with the drug passing into the chamber 16 between the coils of conductor 11 at the location between the end of the extension 20 of the electrode 13 and the seal 22. After the chamber 16 is charged and the lead implanted, body fluids will enter the chamber 17 through the semi-permeable membrane 19 to impart a pressure on the chamber 16 via the impermeable membrane 18. This will result in a dispensing of the drug stored within the chamber 16 through the extension 20 of the electrode 13 and the electrode 13.

Figure 4:
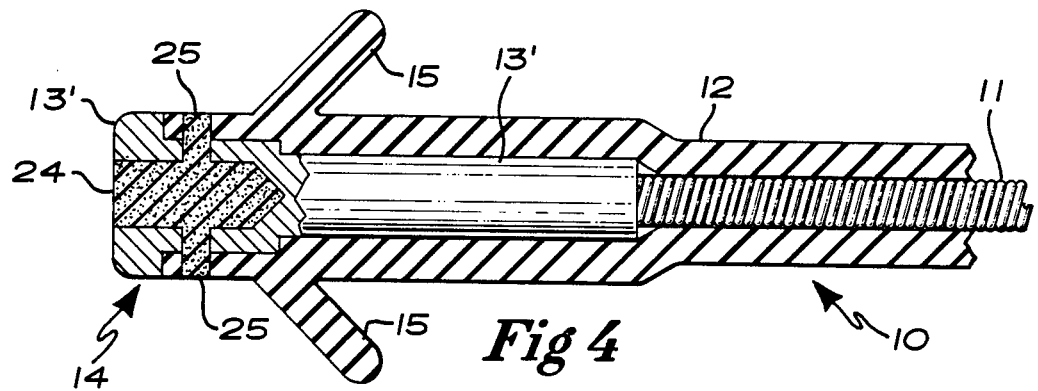
FIGS. 4–6 illustrate alternative preferred embodiments viewed along the line 4—4 in FIG. 3.
Figure 5:
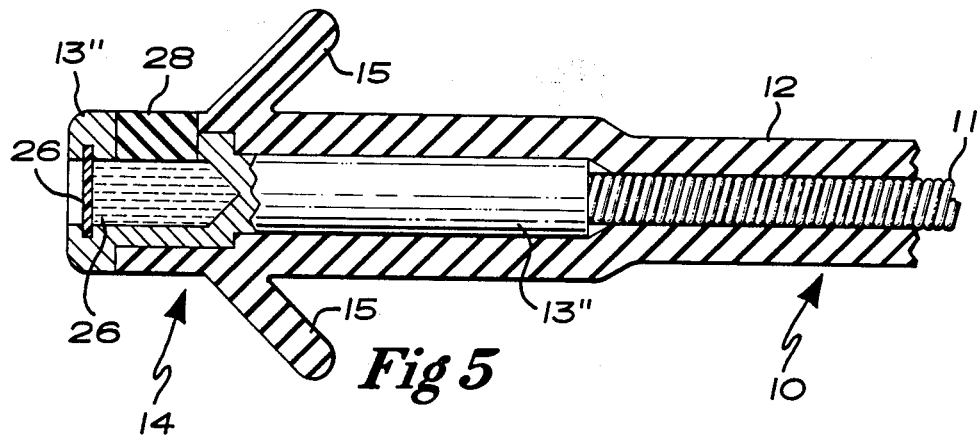
Figure 6:
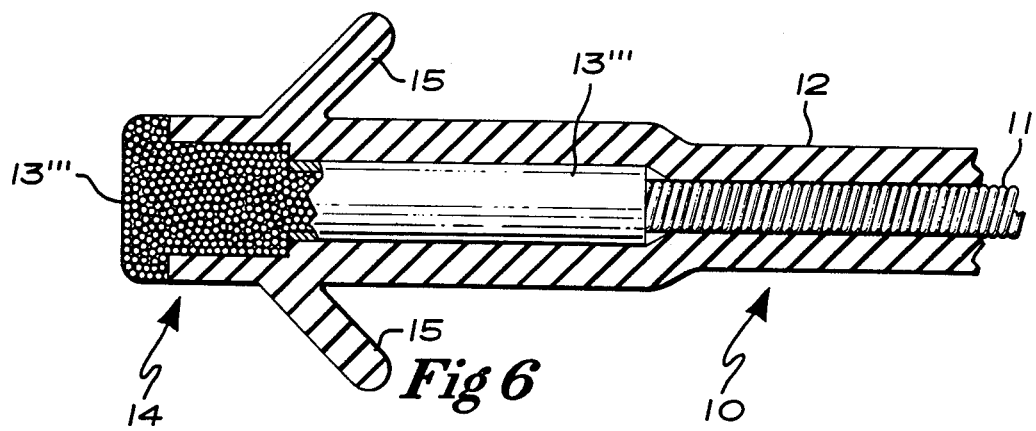

FIG. 3 illustrates the outward configuration of a portion of a lead constructed in accordance with the preferred embodiments of FIGS. 4-6. Throughout the figures, like reference numerals indicate like elements including lead body 10, formed of conductor 11 and sheath 12, and tines 15. A distal tip electrode 13 is indicated generally at 13 in FIG. 3 as is a drug dispenser 14.

Referring now to FIG. 4, there is illustrated a preferred embodiment of the present invention as viewed along the line 4—4 in FIG. 3. A tip electrode 13' is carried at the distal end of the lead and has a central bore which is filled with a solid material 24 which will be discussed more fully below. The electrode 13' extends from the distal end of the lead into electrical communication with the conductor 11. Electrical communication between the electrode 13' and conductor 11 may be established and maintained in any known manner.

Material 24 within the central bore in electrode 13' is a complete material formed by compounding the drug to be dispensed, in solid form, with a sold material suitable for use as a carrier so as to form a permeable structure that allows the body fluids to enter and extract the stored drug. For this purpose, the compounded drug must be water soluble. The carrier material may be a suitable silicone that is compounded with the drug to be dispensed and then placed in the central bore in the electrode 13'. The drug may be dispensed through the electrode 13' from the central bore of the electrode 13'. Additionally, ports may be provided between the central bore of electrode 13' to the sheath of the lead or side of the electrode as indicated at 25 to provide additional dispensing locations adjacent the electrode 13'. Alternatively, the central bore through the electrode 13' may be plugged with the dispensing being accomplished through the ports 25. Any number of ports 25 may be employed.

FIG. 5 illustrates yet another preferred embodiment of the present invention as viewed along the line 4—4 in FIG. 3. In the embodiment of FIG. 5, a tip electrode 13" again has a central bore. However, in the embodiment of FIG. 5 that bore is closed by a semi-permeable membrane 26. Closing of the bore in electrode 13" by the membrane 26 forms a reservoir 27 for drug storage within the bore. An access port 28 is provided through the sidewall of the seath to allow access to the reservoir 27. The member forming the access port 28 may be a self-sealing material such as silicone rubber which may be penetrated, as by a syringe, to charge the reservoir 27 while sealing the puncture from the syringe on withdrawal, in known manner. The reservoir 27 may be charged with any suitable drug that it is desired to dispense and which has a molecular structure that will allow passage through the semi-permeable membrane to be dispensed by diffusion, in known manner.

FIG. 6 illustrates yet another preferred embodiment of the present invention as viewed along the line 4—4 in FIG. 3. In FIG. 6, the electrode 13'" is formed of a sintered material, titanium, for example. Sintering of the electrode material provides a high surface area on which the drug to be dispensed may be deposited for storage as a coating. The sintered electrode may be coated with the drug to be dispensed at the time of manufacture. Alternatively, the coating may be selectively applied at or prior to the time of implant of the lead.

Obviously, many modifications and variations of the present invention are possible in light of the above teachings. For example, FIG. 4 discloses an embodiment wherein the drug to be dispensed is compounded so as to form a composite material. That same process may be employed to form a composite material which may be employed to form the sheath 12 of the lead, the tines 15 or both. Also, while drugs to accomplish specific purposes are discussed herein, the invention is not limited to drugs that are useful to accomplish only those purposes. Further, apart from forming a part of the delivery system for the electrical stimulation energy, the particular conductor and sheath configurations form no part of the present invention. Indeed, the disclosed electrode configurations may be varied without departing from the scope of the present invention. It is therefore to be understood that, within the scope of the appended claims, the invention may be practiced otherwise than as specifically described.

What is claimed is:

1. In a body implantable lead for the delivery of stimulation energy to a desired body site of the type having at least one electrode carried by the lead, said electrode being adapted for positioning at least adjacent to said desired body site, the improvement wherein said lead further comprises drug dispensing means carried by said lead and includes means for storing a drug to be dispensed while allowing dispensing of said drug at least adjacent the distal end of said lead to counter undesirable interactions between said lead and the body and wherein said drug is compounded into a solid material, said solid material being carried by said lead adjacent said distal end.

2. The body implantable lead of claim 1 wherein said solid material forms at least a portion of the body of said lead.

3. The body implantable lead of claim 1 wherein said drug is compounded into a solid material, said solid material being carried by said lead at least partially within said tip electrode.

* * * * *

REEXAMINATION CERTIFICATE (2320th)

United States Patent [19]

Stokes

[11] B1 4,711,251

[45] Certificate Issued  Jun. 28, 1994

[54] BODY IMPLANTABLE LEAD

[75] Inventor: Kenneth B. Stokes, Minneapolis, Minn.

[73] Assignee: Medtronic, Inc., Minneapolis, Minn.

Reexamination Request:
No. 90/002,494, Sep. 10, 1991

Reexamination Certificate for:
Patent No.: 4,711,251
Issued: Dec. 8, 1987
Appl. No.: 480,913
Filed: Mar. 31, 1983

Related U.S. Application Data

[63] Continuation of Ser. No. 182,963, Sep. 2, 1980, abandoned.

[51] Int. Cl.$^5$ .............................................. A61N 1/05
[52] U.S. Cl. .................................... 607/116; 604/20; 604/890.1; 604/892.1
[58] Field of Search ................................. 128/784–786

[56] References Cited

U.S. PATENT DOCUMENTS

| | | | |
|---|---|---|---|
| 3,680,544 | 8/1972 | Shinnick | 128/419 P |
| 3,932,656 | 1/1976 | Ramwell et al. | 424/16 |
| 4,033,357 | 7/1977 | Helland et al. | 128/418 |
| 4,101,984 | 7/1978 | MacGregor | 3/1.5 |

OTHER PUBLICATIONS

Folkman, Judah et al., *Drug Pacemakers in the Treatment of Heart Block*, Annals of the New York Academy of Sciences, vol. III, Art. 3, pp. 857–868, 1964.

*Primary Examiner*—William E. Kamm

[57] ABSTRACT

A body implantable lead for the delivery of stimulation energy to a desired body site including a drug dispenser carried by the lead which retains a drug to be dispensed while allowing a dispensing of that drug at least adjacent the desired body stimulation site. The drug may be one which is intended to counter thrombus formation, fibrosis, inflammation or arrhythmias, or any combination thereof, or to accomplish any other localized purpose. The drug may be in liquid form retained in a reservoir carried by the lead with an agency controlling dispensing of the drug. The controlling agency may be a semi-permeable membrane. Alternatively, the reservoir may be formed as an osmotic pump. As a further alternative, the drug may be retained as a coating on a large surface area portion of the lead, or an electrode carried by the lead. In a preferred embodiment, the drug is compounded into a solid material which is carried by the lead while being exposed to body tissues and flesh and fluids at least adjacent the desired stimulation site.

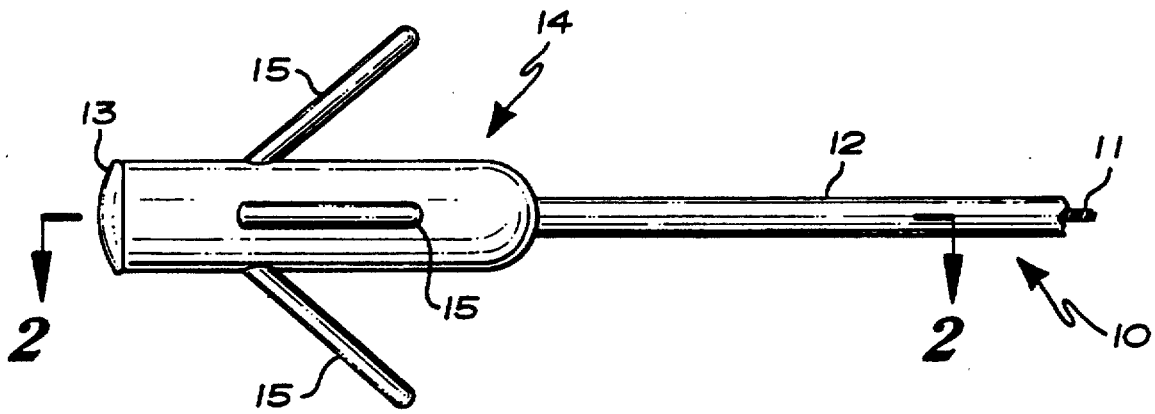

REEXAMINATION CERTIFICATE ISSUED UNDER 35 U.S.C. 307

THE PATENT IS HEREBY AMENDED AS INDICATED BELOW.

Matter enclosed in heavy brackets [] appeared in the patent, but has been deleted and is no longer a part of the patent; matter printed in italics indicates additions made to the patent.

AS A RESULT OF REEXAMINATION, IT HAS BEEN DETERMINED THAT:

Claim 2 having been finally determined to be unpatentable, is cancelled.

Claims 1 and 3 are determined to be patentable as amended.

New claims 4 and 5 are added and determined to be patentable.

1. In a body implantable lead for the delivery of stimulation energy to a desired body site, of the type having at least one electrode carried by the lead, said electrode being adapted for positioning at least adjacent said desired body site, the improvement wherein *said electrode comprises an electrically conductive portion exposed to the exterior of said lead for directly contacting said desired body site, and* said lead further comprises *a drug to be dispensed and* drug dispensing means carried by said lead and includes means for storing [a] *said* drug to be dispensed while allowing dispensing of said drug at least adjacent the distal end of said lead, *adjacent said exposed conductive electrode portion,* to counter undesirable interactions between said lead and [the] *said* body *site,* and wherein said drug is compounded into a solid material, said solid material being carried by said lead adjacent said distal end.

3. [The body implantable lead of claim 1] *In a body implantable lead for the delivery of stimulation energy to a desired body site, of the type having at least one tip electrode carried by the lead, said electrode being adapted for positioning at least adjacent said desired body site, the improvement wherein said lead further comprises a drug to be dispensed and drug dispensing means carried by said lead and includes means for storing said drug to be dispensed while allowing dispensing of said drug at least adjacent the distal end of said lead to counter undesirable interactions between said lead and said body site, and wherein said drug is compounded into a solid material, said solid material being carried by said lead adjacent said distal end* [wherein said drug is compounded into a solid material], said solid material being carried by said lead at least partially within said tip electrode.

*4. In a body implantable lead for the delivery of stimulation energy to a desired body site, of the type having at least one electrode carried by the lead, said electrode being adapted for positioning at least adjacent said desired body site, the improvement wherein said electrode comprises an electrically conductive portion exposed to the exterior of said lead for directly contacting said desired body site, and said lead further comprises a drug to be dispensed and drug dispensing means carried by said lead and includes means for storing said drug to be dispensed while allowing dispensing of said drug at least adjacent the distal end of said lead through said exposed conductive electrode portion to counter undesirable interactions between said lead and said body site, and wherein said drug is compounded into a solid material, said solid material being carried by said lead adjacent said distal end.*

*5. In a body implantable lead for the delivery of stimulation energy to a desired body site, of the type having at least one electrode carried by the lead, said electrode being adapted for positioning at least adjacent said desired body site, the improvement wherein said lead further comprises a drug to be dispensed, said drug comprising means for countering undesirable interactions between said lead and said body site, and wherein said lead comprises drug dispensing means carried by said lead, and includes means for storing said drug to be dispensed while allowing dispensing of said drug at least adjacent the distal end of said lead to counterundesirable interactions between said lead and said body site, and wherein said drug is compounded into a solid material, said solid material being carried by said lead adjacent said distal end.*

* * * * *